United States Patent
Tai et al.

(10) Patent No.: US 9,108,024 B2
(45) Date of Patent: Aug. 18, 2015

(54) RETENTION COMPONENT FOR PLACEMENT OF ENTERAL FEEDING TUBES

(71) Applicant: AVENT, INC., Alpharetta, GA (US)

(72) Inventors: Kok-Ming Tai, Lawrenceville, GA (US); Alison S. Bagwell, Alpharetta, GA (US); Donald J. McMichael, Roswell, GA (US); Neil M. Becker, Roswell, GA (US); Benone Tarcau, Lawrenceville, GA (US)

(73) Assignee: Avent, Inc., Alpharetta, GA (US)

( * ) Notice: Subject to any disclaimer, the term of this patent is extended or adjusted under 35 U.S.C. 154(b) by 255 days.

(21) Appl. No.: 13/674,514

(22) Filed: Nov. 12, 2012

(65) Prior Publication Data

US 2014/0094751 A1   Apr. 3, 2014

Related U.S. Application Data

(60) Provisional application No. 61/707,318, filed on Sep. 28, 2012.

(51) Int. Cl.
| | | |
|---|---|---|
| *A61M 29/00* | (2006.01) | |
| *A61M 29/02* | (2006.01) | |
| *A61M 25/10* | (2013.01) | |
| *A61J 15/00* | (2006.01) | |

(52) U.S. Cl.
CPC ............ *A61M 29/02* (2013.01); *A61J 15/0042* (2013.01); *A61J 15/0049* (2013.01); *A61M 25/1002* (2013.01); *A61M 25/1011* (2013.01)

(58) Field of Classification Search
CPC .............. A61J 15/0015; A61J 15/0019; A61J 15/0023; A61J 15/0026; A61J 15/003; A61J 15/0034; A61J 15/0042; A61J 15/004; A61J 15/0046; A61J 15/0049; A61J 15/0069; A61M 25/10; A61M 25/1002; A61M 25/1011; A61M 25/1013; A61M 25/1047; A61M 25/1061; A61M 29/00; A61M 29/02
USPC ........ 604/103.03, 103.07; 606/191, 192, 197, 606/198
See application file for complete search history.

(56) References Cited

U.S. PATENT DOCUMENTS

| | | | | |
|---|---|---|---|---|
| 3,915,171 | A * | 10/1975 | Shermeta | 604/101.05 |
| 5,234,454 | A * | 8/1993 | Bangs | 606/191 |
| 5,743,852 | A * | 4/1998 | Johnson | 600/207 |
| 6,019,746 | A | 2/2000 | Picha et al. | |
| 8,177,742 | B1 | 5/2012 | Bagwell et al. | |
| 2009/0312701 | A1 * | 12/2009 | Gobel et al. | 604/96.01 |
| 2012/0078174 | A1 | 3/2012 | Tai et al. | |

FOREIGN PATENT DOCUMENTS

| | | |
|---|---|---|
| WO | WO 2006/133927 A2 | 12/2006 |
| WO | WO 2009/135166 A2 | 11/2009 |

* cited by examiner

*Primary Examiner* — Nicholas Lucchesi
*Assistant Examiner* — Leah Stohr
(74) *Attorney, Agent, or Firm* — Dority & Manning, P.A.

(57) ABSTRACT

The present disclosure provides an innovative retention element for use with feeding tubes for placement in a gastric lumen, desirably under direct visualization using an endoscope. The retention balloon has a shape with a recessed or concave center that provides space to accommodate the distal end of inserted feeding tubes. The retention balloon may be conical, square and half spherical and holds the stomach against the inner abdominal wall.

9 Claims, 5 Drawing Sheets

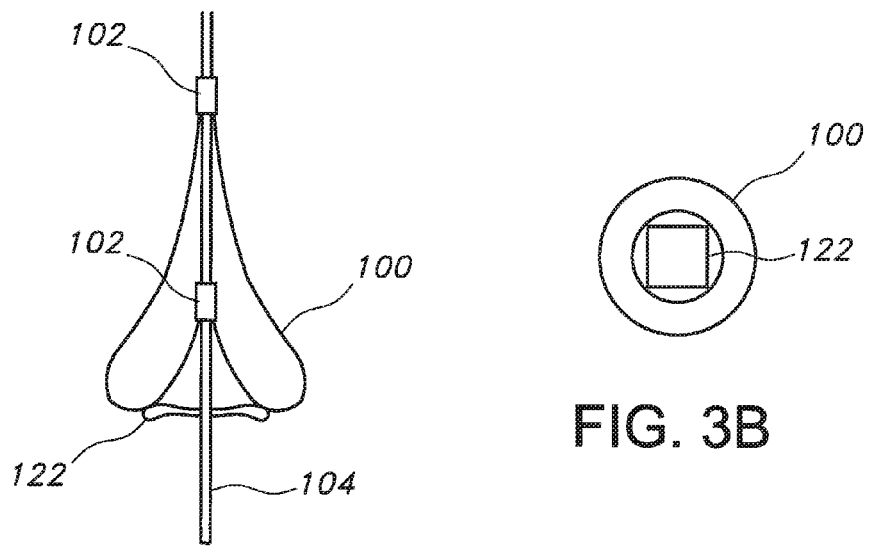
FIG. 3A
FIG. 3B
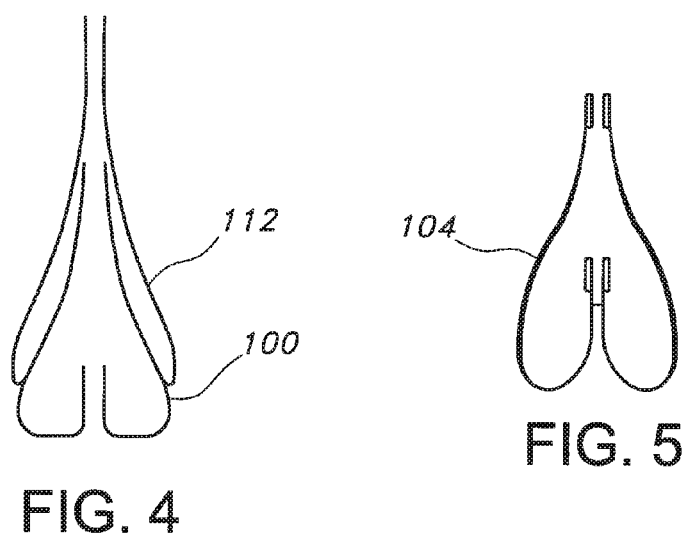
FIG. 4
FIG. 5

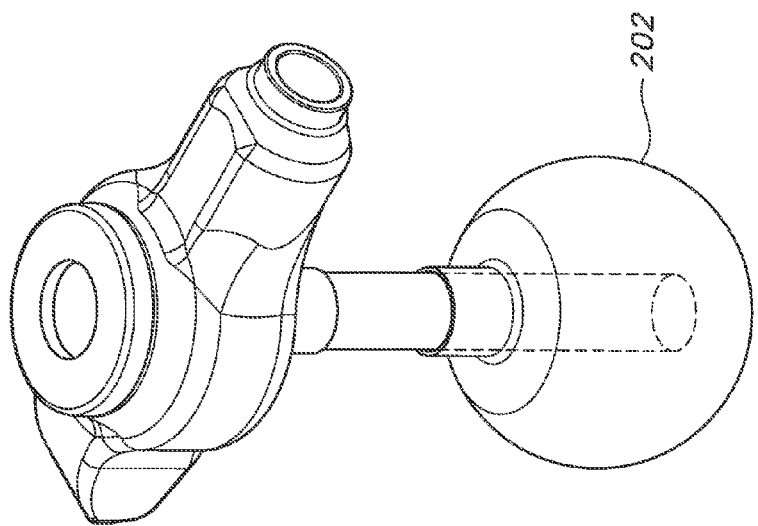
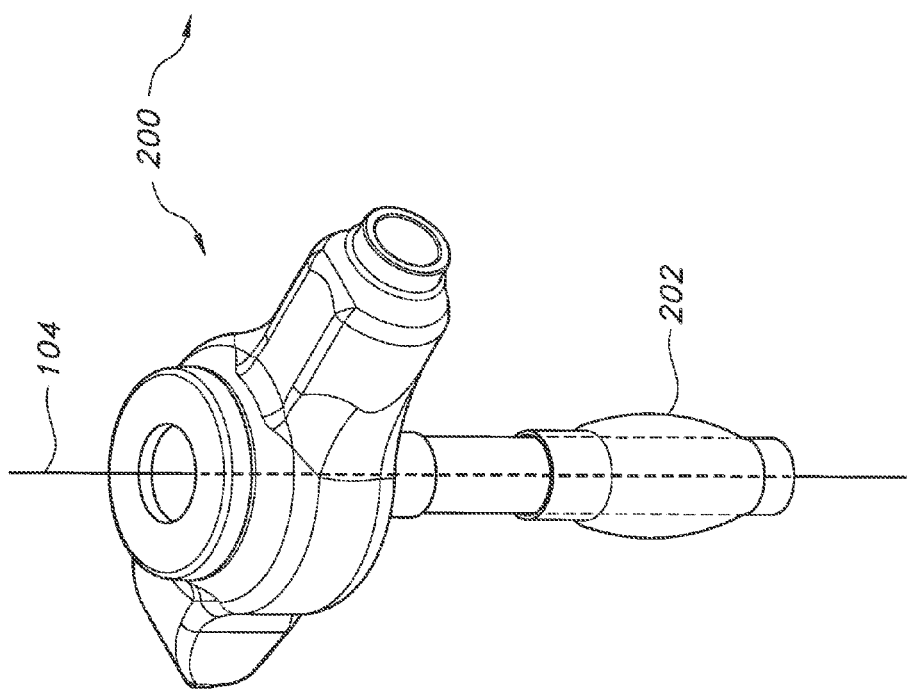

RETENTION COMPONENT FOR PLACEMENT OF ENTERAL FEEDING TUBES

This application claims priority from U.S. Provisional Application 61/707,318 filed on Sep. 28, 2012.

The present disclosure relates to catheters such as feeding tubes and their placement in the body of a patient.

Numerous situations exist in which a body cavity needs to be catheterized to achieve a desired medical goal. One relatively common situation is to provide nutritional solutions or medicines directly into the stomach or intestines. A stoma is formed in the stomach or intestinal wall and a catheter is placed through the stoma. This surgical opening and/or the procedure to create the opening is commonly referred to as "gastrostomy". Feeding solutions can be injected through the catheter to provide nutrients directly to the stomach or intestines (known as enteral feeding). A variety of different catheters intended for enteral feeding have been developed over the years, including some having a "low profile" relative to the portion of the catheter which sits on a patient's skin, as well as those having the more traditional or non-low profile configuration. These percutaneous transconduit catheters (sometimes referred to as "percutaneous transconduit tubes") are frequently referred to as "gastrostomy catheters", "percutaneous gastrostomy catheters", "PEG catheters" or "enteral feeding catheters". U.S. Pat. No. 6,019,746 for a "Low Profile Balloon Feeding Balloon" issued to Picha et al. on Feb. 1, 2000, provides an example of one balloon.

These catheters are frequently placed in a procedure called percutaneous endoscopic gastrostomy (frequently referred to as PEG). Traditionally, a PEG tube is placed using endoscopic guidance or x-ray guidance. In a conventional PEG procedure that places a PEG tube into a patient's stomach, an endoscope is used to observe that the patient's esophagus is unobstructed and to inspect and inflate the stomach to see that the area selected for the gastrostomy can be distended. If the location is suitable, this spot is selected.

A needle is inserted into the patient in the area in the appropriate location where a small incision may be made in the skin. An endoscopist will then typically watch through the endoscope as a needle pushes through the patient's skin, through the abdominal wall, and into the gastric lumen in the selected area to form a needle tract. A guide wire is passed through the needle into the gastric lumen (e.g. the stomach). The endoscopist will use an endoscopic snare to grasp the guide wire firmly. The snare, passed through the working channel of the endoscope, firmly grabs the guide wire. Both the endoscope and snare are then withdrawn together through the patient's mouth, pulling the guide wire with them. The end of the guide wire that extends out from the patient's mouth is subsequently attached to a retention element and the other end of the guide wire remains outside the patient's skin in the abdominal region. The retention element is guided into the patient's mouth (typically while the endoscope is completely removed from the patient) and pulled into the patient's gastric lumen as the guide wire is pulled from the end that remains outside the patient's skin. Once the retention element is in the gastric lumen, it is pulled snugly against the abdominal wall at the point of the stoma.

After suitable dilation of the stoma, a feeding tube may be inserted through the stoma while the stomach held snugly against the abdominal wall. The feeding tube has a retainer on the distal end that may be expanded within the stomach after the distal end of the feeding tube is inserted. One suitable feeding tube is described in U.S. patent application Ser. No. 13/245,542, filed Sep. 26, 2011, (publication US 2012/0078174A1) and commonly assigned. The '542 feeding tube does not use an inflatable balloon as the retainer. Another suitable feeding tube is shown in U.S. Pat. No. 8,177,742 and uses an inflatable balloon as the retainer.

Sometimes during the insertion and unfurling or inflation of the feeding tube retainer, the retention element is in the way of the expandable retainer of the feeding tube and the retention element must be deflated or pushed out of the way in order to completely insert the distal end of the feeding tube. This can result in additional trauma to the patient and perhaps in the inability to insert this type of retainer successfully.

Accordingly, there is a need for improved retention elements that permit a user or health care provider to quickly and easily place feeding tubes through the patient's stoma and into a body lumen, such as, for example, a stomach lumen. Such a retention element should cooperate with a retainer and is designed to retain its position yet still allow the feeding tube to be inserted. The retention element should not get in the way of the expandable retainer of the feeding tube as the tube is inserted.

SUMMARY

In response to the difficulties and problems discussed herein, the present disclosure provides an innovative retention component for use with feeding tubes for placement in a gastric lumen, desirably under direct visualization using an endoscope. The retention component has a balloon desirably having an inflated shape with a recessed or concave center that provides space to accommodate the distal end of inserted feeding tubes. The retention component holds the stomach against the inner abdominal wall.

BRIEF DESCRIPTION OF THE DRAWINGS

FIG. 3A is a cross-sectional view of an inflated retention component having a tie reinforcement.

FIG. 3B is a view of the proximal end of the retention balloon shown in FIG. 3A, showing the ties holding the balloon together.

FIG. 4 is a cross-sectional view of an inflated retention component having a skirt structure for reinforcement of the retention balloon.

FIG. 5 is a cross-sectional view of an inflated retention component having stiffer walls (indicated by darkened side lines) to provide reinforcement for the retention component.

FIGS. 7A and 7B show a conventional enteral feeding tube having a balloon retainer in the un-inflated and inflated states, respectively.

DETAILED DESCRIPTION

Figure 1:
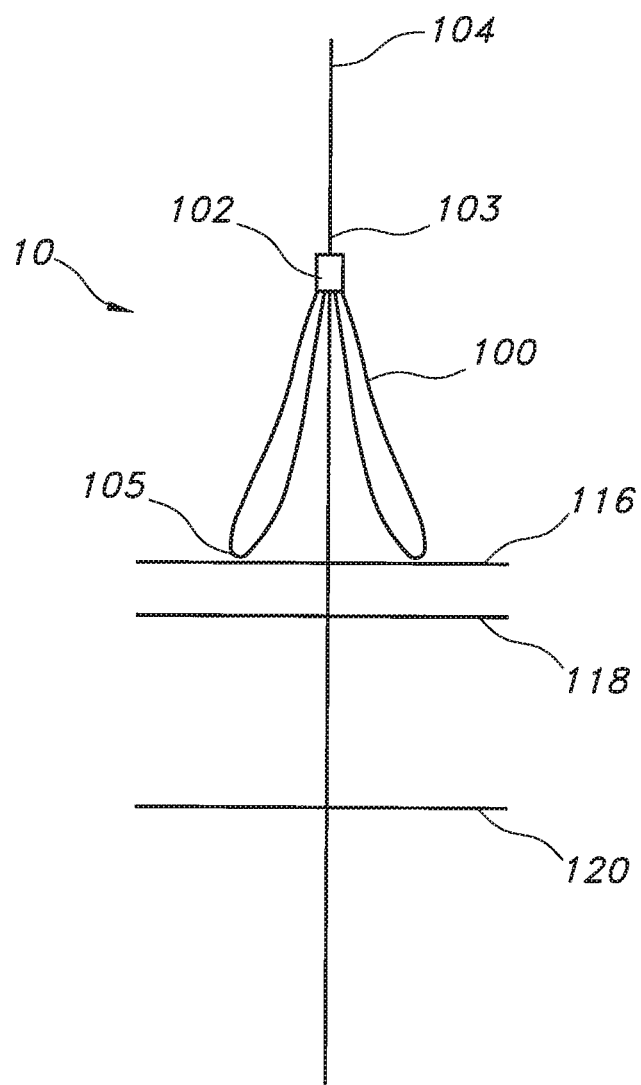
FIG. 1 is a drawing showing the retention component in cross-section on a guide wire in position within a stomach that has been pulled snugly against the inner abdominal wall.

Reference will now be made in detail to one or more embodiments, examples of which are illustrated in the drawings. It should be understood that features illustrated or described as part of one embodiment may be used with another embodiment to yield still a further embodiment.

Since the stomach is a common example of a gastric lumen, for the purpose of describing the present disclosure, the use of the term "stomach" is representative of all other gastric lumens or spaces (e.g. duodenum, jejunum, ileum, etc.), unless otherwise specified.

The function of the retention component 10 is to maintain the stomach (or other gastric lumens) against the abdominal wall during and after placement of an enteral feeding tube. FIG. 1 shows the retention balloon 100 on the structural support 104 in place with the stomach wall 116 snugly against the inner abdominal wall 118.

Figure 2:
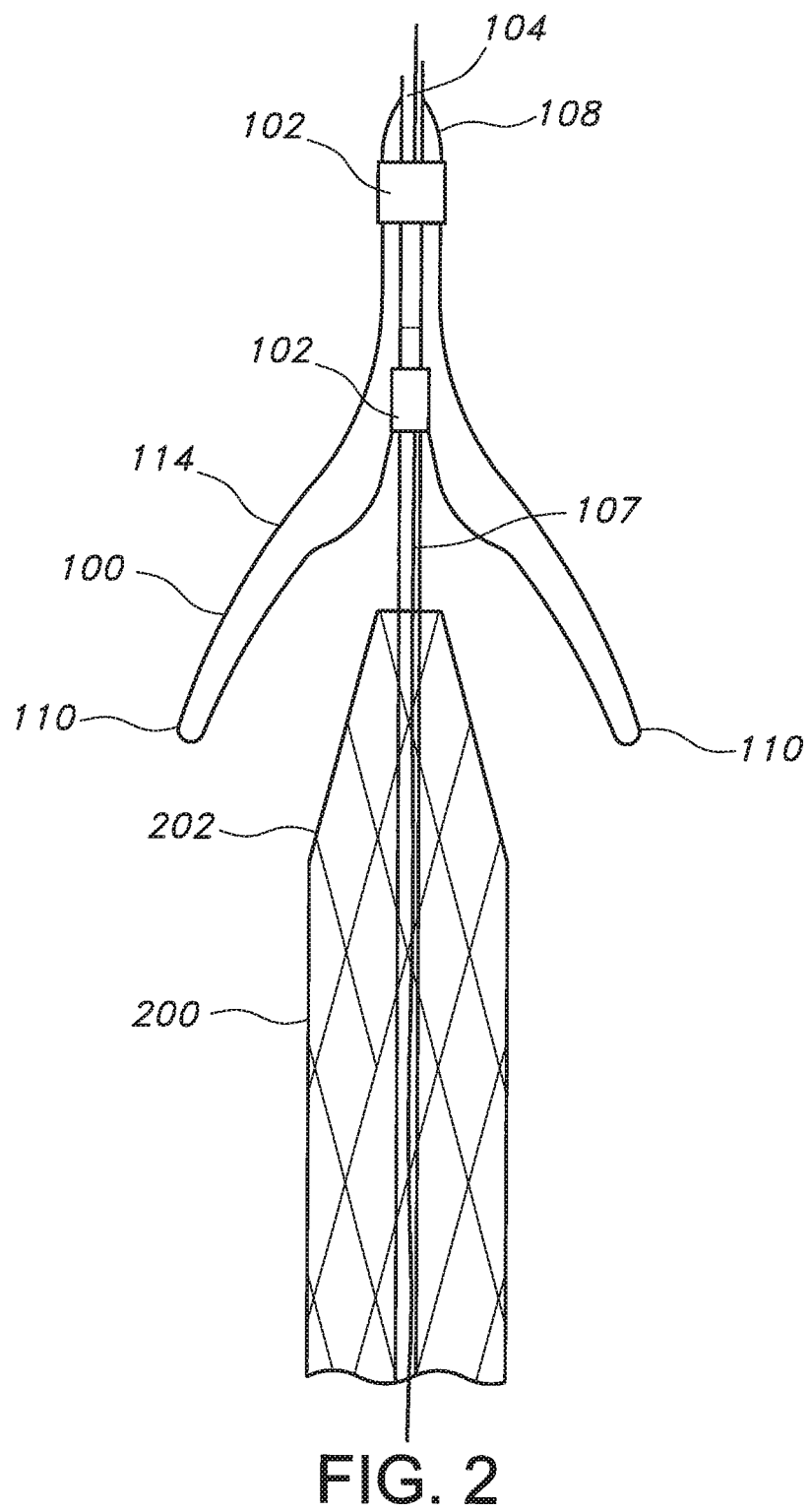
FIG. 2 is a cross-sectional view of an inflated retention component and feeding tube showing the relationship of the two as the feeding tube is inserted.

As shown in FIG. 1, the retention component 10 has an inflatable retention balloon 100 on a structural support 104. The retention balloon 100 has at least one collar 102 on or near a distal 103 or proximal 105 end or between them, though desirably has two collars 102 as shown in FIG. 2. The balloon 100 desirably has an inflated conical shape that results in a concavity at the proximal end 105 of the balloon 100. The concavity is desirably concentric.

The structural support 104 is elongated relative to the balloon 100 and may have an inflation lumen 107 in fluid communication with the balloon 100 so that the balloon 100 may be inflated and deflated as needed. The structural support 104 may be a cannula, stylet, rod or other support that may be used to move the balloon 100 as desired. The structural support 104 may be flexible or rigid or a combination of flexible and rigid sections as may be needed in a particular installation.

The feeding tube 200 is guided and advanced over the structural support 104 into the stoma (FIG. 2). The inflated retention balloon 100 allows room for the retainer 202 of the feeding tube to enter the stomach. The retainer 202 can be deployed to hold the feeding tube in place as is conventionally known. The retention balloon 100 may then be deflated and removed from the patient. FIG. 7A shows a feeding tube 200 having an inflatable bumper or retainer 202 on the distal end. The feeding tube 200 is advanced over the structural support 104 while the retainer 202 is in its collapsed or insertion state, e.g. deflated for inflatable retainers, radially contracted for rigid retainers. Once the retainer 202 is in position in the stomach, the retainer 202 can be deployed, e.g. inflated (FIG. 7B) or radially extended. The deployed retainer 202 holds the stomach against the inner abdominal wall, and the retention balloon 100 may be removed. Installation of the feeding tube 200 is now complete and the feeding tube 200 may be placed in service.

As can be seen from the Figures, the generally conical retention balloon 100 when inflated has a cone apex 108, a cone base 110, and lateral surfaces or a wall 114 therebetween connecting the apex 108 and base 110. As noted above, the balloon 100 is generally conical in shape, allowing for a recessed, concave center that provides space for the retainer 202 of the feeding tube 200. It should be noted that although a conical embodiment is shown, a box-shaped or hemispherical shape would also function. The retention component holds the stomach against the inner abdominal wall while still allowing space in the recessed center to accommodate the distal end of subsequently inserted components.

It has been found that the inflated shape of the retention balloon 100 can sometimes result in the balloon base 110 and wall 114 folding backwards onto itself. "Folding backwards" means the part of the balloon that contacts the inner wall of the stomach, the base 110, can fold towards the apex 108 of the balloon 100. This can occur if an excessive amount of force is used to pull the retention balloon 100, and hence the stomach, towards the inner abdominal wall. Should the retention balloon 100 fold backwards, the space for the feeding tube may be lost. FIGS. 3, 4 and 5 provide possible solutions to this problem.

FIG. 3A illustrates the use of a "ties" 122 that provide dimensional support upon inflation to the base 110 by connecting between points on the base 110 while allowing space for the retainer 202 of the feeding tube to pass into the concavity. These reinforcement ties, e.g. cords, mesh webbing, or an apertured disc, are flexible but not extensible. FIG. 3B is an end view drawing of the proximal end of the inflated balloon 100 and shows an embodiment of the ties 122 that do not cross the center of the balloon 100 but connect to the balloon 100 so that access to the center is not blocked, e.g. diagonally.

FIG. 4 shows an embodiment in which a second balloon 112 over the original retention balloon 100 acts as a skirt to provide conical shape retention for the balloon 100. The second balloon 112 is a partially enveloping sleeve or skirt that to forces the balloon 100 to achieve an inflated conical shape. Another skirt embodiment is a non-inflating sleeve in place of balloon 112; this non-inflating sleeve can be a cylinder that deforms to have a larger end in the proximal direction upon inflation of retention balloon 100, or the sleeve can be pre-shaped to have one end larger than the other with the larger end positioned proximally.

FIG. 5 shows yet another way of providing strength to the balloon 100 by making the side walls 114 of the balloon 100 between the apex 108 and the base 110 stiffer (indicated by darker lines). Stiffening the walls 114 may be accomplished through the use of a stiffer polymer than the balance of the balloon 100 or by making the walls thicker than the base and/or apex or both.

Use of non-compliant or semi-compliant materials and known shaping techniques (e.g. blow molding within pre-shaped cavities) can contribute to the conical shape of the balloon 100 between the collars 102. Positioning of collars 102 on the structural support 104 further contributes to the conical shape. FIG. 2 shows the collar 102 at the distal end 102 of the balloon 100 attached to the structural support 104 so there is no overlapping of the balloon 100 while the more proximally placed collar of the balloon 100 is attached to the structural support so that the balloon inverts over the collar.

Figure 6:
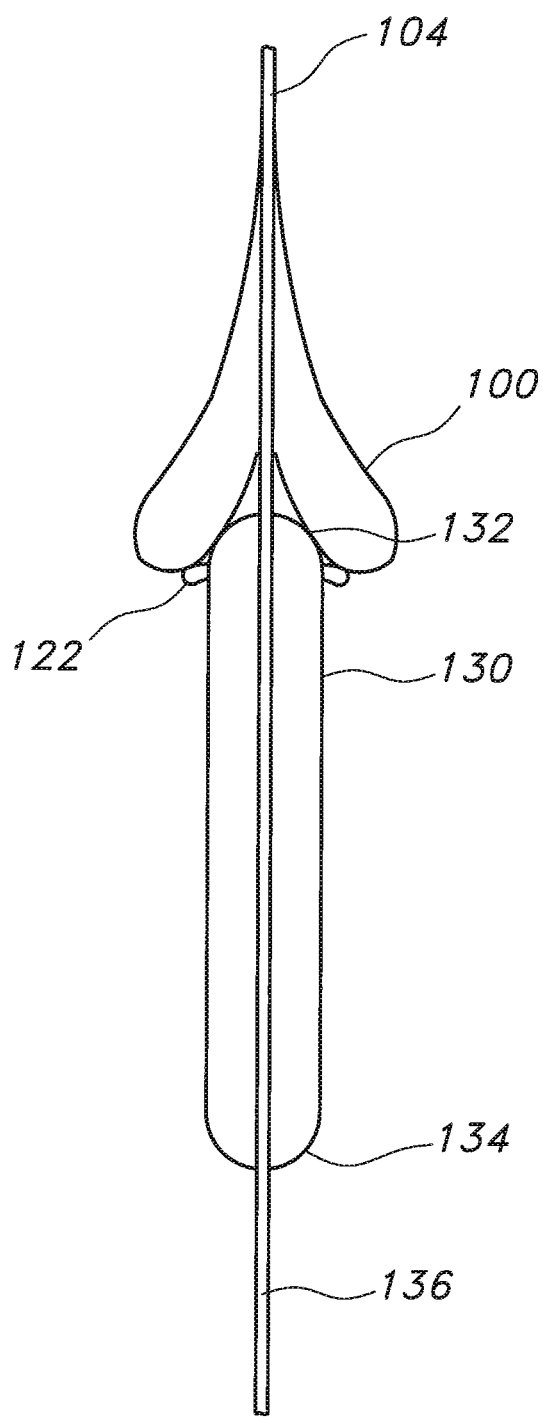
FIG. 6 shows the retention component with a dilation balloon nesting within the concentric concavity of its proximal end.

The component 10 may include an inflatable dilation balloon 130 or be configured for positioning an inflatable dilation balloon 130 adjacent the retention balloon 100, as shown in FIG. 6. When the component 10 includes a dilation balloon 130, the dilation balloon 130 is supported on the structural support 104. When the dilation balloon 130 is a separate component it is configured to be positioned over the structural support 104. Whether included with the component 10 or provided separately, the dilation balloon 130 has two opposing ends where one (distal) end 132 is configured to at least partially nest within the concavity of the inflated retention balloon 100. The dilation balloon 130 should have a uniform inflated diameter along a length between the distal and proximal ends 132, 134 and an opening in fluid communication with an inflation lumen 136.

As described above, a needle is usually used to puncture the skin 120 above the abdomen and place a guide wire in the desired location. This is generally with the use of an endoscope inserted into the patient's stomach so that the initial puncture point can be observed from inside the stomach.

Outside-in Installation:

After insufflation of the stomach, the retention component 10 is percutaneously inserted into the stomach while the proximal end of the structural support 104 remains outside the body. The dilation balloon 130 is positioned so that the end 132 intended for nesting within the concavity of the retention balloon 100 is percutaneously inserted into the stomach and the other end 134 remains outside the body without completely covering the proximal end of the structural support 104. The retention balloon 100 is inflated and a tractive (drawing) force is applied to the proximal end of the structural support 104 to draw the proximal end 105 of the inflated retention balloon 100 against the stomach. The dilation balloon 130 is inflated to enlarge the insertion tract to a defined stoma and then deflated. An enteral feeding tube 200 with its retainer 202 in the insertion state (i.e. furled, collapsed, or deflated) is inserted over the structural support 104, over the deflated dilation balloon 130, through the stoma and into the concavity of the inflated retention balloon 100. The retainer 202 is deployed to a retention state (unfurled, extended, or inflated) within the concavity and the tube 200 is positioned so that the retainer 202 is against the stomach wall. The retention balloon 100 is deflated to release the tractive force. The structural support 104, the retention component 10 and any other placement devices (e.g. dilation balloon 130) are removed through the tube 200.

When the retention component 10 is used to place a feeding tube 200 with a non-inflatable retainer or bumper 202, there is no need for gastropexy fasteners to aid in maintaining the stomach in apposition with the abdominal wall until these tissue structures fuse together. Feeding tubes 200 with such bumpers 202 have sufficient dimensional stability to maintain apposition of the stomach against the abdominal wall. When the retainer 202 is of the inflatable type, gastropexy is recommended to retain the stomach against the abdominal wall.

When the retention component 10 is used to place a feeding tube 200 with an inflatable retainer 202 or bumper, the retention balloon 100 may be left inflated around the inflated bumper 202 to maintain the stomach in apposition with the abdominal wall until these tissue structures fuse together sufficiently. After the apposition force provided by the retention component 10 is no longer needed, the retention balloon 100 may be deflated and the component 10 removed.

Inside-out Installation:

The retention component 10 may be placed from within the stomach through a percutaneous incision via the aid of a conventional guide wire. For such inside-out placement, a guide wire traversing through a percutaneous incision, the stomach, and the esophagus to outside of the mouth is attached to the proximal end of the structural support 104. The endoscopic snare may be used to pull the guide wire. The guide wire is pulled back out through the incision and so pulls the retention component 10 into the stomach and through the incision until the retention component 10 is positioned as described above. The balance of the installation is the same as above.

Whether the "outside-in" or "inside-out" procedure is used, once the retention balloon 100 is successfully in place and inflated as shown in FIG. 1 and the stoma is dilated, the feeding tube 200 may be placed.

In the practice of the disclosure the feeding tube 200 may have a tube size varying from about 4 to 6 French. The width of the base 110 of the inflated retention balloon 100 is larger than the size of the feeding tube retainer 202 (as shown in FIG. 2) and may be between 26 and 28 French to allow for the deployment of the retainer 202 of the feeding tube component 10. (Note, French is a measure of circumference based on the theory that non-round tubes of the same circumference will fit into the same incision. One French is approximately 0.33 mm or 0.013 inch). The balloon 100 may be made from any suitable polymer. Typical polymers include polyesters, polyurethanes, nylons, and polyolefins like polyethylene, polypropylene and polybutylene.

While the present disclosure has been described in connection with certain preferred embodiments it is to be understood that the subject matter encompassed by way of the present disclosure is not to be limited to those specific embodiments. On the contrary, it is intended for the subject matter of the disclosure to include all alternatives, modifications and equivalents as can be included within the spirit and scope of the following claims.

We claim:

1. A retention component for medical procedures comprising an inflatable retention balloon with distal and proximal ends on a structural support, the retention balloon having at least one collar on a distal or proximal end; the structural support extending distally beyond the distal end of the balloon and having an inflation lumen in fluid communication with the balloon so that the balloon may be inflated and deflated as needed, said balloon having an inflated shape that results in a concavity at the proximal end of the balloon, the concavity extending distally so as to define an open space around the structural support between the proximal end and distal end of the balloon when the proximal end of the balloon is engaged against a wall of a body cavity in a patient.

2. The retention component of claim 1 wherein said balloon has a shape selected from the group consisting of conical, and half spherical.

3. The retention component of claim 1 wherein said balloon has a shape with an apex at the distal end and base at the proximal end, wherein said base contacts an inner abdominal wall of a patient and wherein the base has a large enough width such that a feeding tube retainer is slidable along the structural support into the concavity.

4. The retention component of claim 3 wherein said balloon has walls between said apex and base and said walls are stiffer than said apex and base.

5. The retention component of claim 1 wherein the balloon is made from a polymer that is non-compliant or semi-compliant.

6. A retention component for medical procedures comprising an inflatable retention balloon with distal and proximal ends on a structural support, the retention balloon having at least one collar on a distal or proximal end; wherein said balloon has an inflated shape that results in a concavity at the proximal end of the balloon, the proximal end of the balloon comprising a base, the concavity extending distally so as to define an open space around the structural support between the proximal end and distal end of the balloon when the proximal end of the balloon is engaged against a wall of a body cavity in a patient and further comprising a tie reinforcement that spans from one point to another point on the base to provide shape retention to the balloon.

7. A retention component for medical procedures comprising an inflatable retention balloon with distal and proximal ends on a structural support, the retention balloon having at least one collar on a distal or proximal end; wherein said balloon has an inflated shape that results in a concavity at the proximal end of the balloon, the concavity extending distally so as to define an open space around the structural support between the proximal end and distal end of the balloon when the proximal end of the balloon is engaged against a wall of a body cavity in a patient and further comprising a skirt around said retention balloon to provide greater shape retention to the balloon.

8. A dilation balloon and a retention balloon for medical procedures comprising:

a conical retention balloon on a structural support with a recessed center at a proximal end of the retention balloon that provides space for accommodating a distal end of an enteral feeding tube component, and;

a separate dilation balloon on the structural support that dilates a stoma, the dilation balloon having a uniform diameter inflated state between an distal end and a proximal end of the dilation balloon such that the distal end of the dilation balloon nests within the recessed center of the retention balloon.

9. The dilation and retention balloon of claim 8 wherein said conical and dilation balloons are connected together and have separate inflation lumens.

\* \* \* \* \*